United States Patent [19]

Näf

[11] 4,192,781

[45] Mar. 11, 1980

[54] PERFUMED ARTICLES CONTAINING CIS-OCT-6-EN-1-AL

[75] Inventor: Ferdinand Näf, Geneva, Switzerland

[73] Assignee: Firmenich SA, Geneva, Switzerland

[21] Appl. No.: 932,700

[22] Filed: Aug. 10, 1978

Related U.S. Application Data

[62] Division of Ser. No. 765,056, Feb. 2, 1977, Pat. No. 4,132,675.

[30] Foreign Application Priority Data

Feb. 11, 1976 [CH] Switzerland .......................... 164/576

[51] Int. Cl.$^2$ ................................................ A61K 7/46
[52] U.S. Cl. ................................ 252/522 R; 424/333; 426/534; 260/601 R; 252/174.11

[58] Field of Search ........................... 252/522, 174.11; 424/333; 260/601 R

[56] References Cited

PUBLICATIONS

Arctader, Steffen, "Perfume & Flavor Chemicals", (1969), published by Author, Monograph 124.
LeBel et al., "J. Am. Chem. Soc.", vol. 86 (1964), pp. 3759–3767.

*Primary Examiner*—V. D. Turner
*Attorney, Agent, or Firm*—Pennie & Edmonds

[57] ABSTRACT cis-Oct-6-en-1-al is a novel unsaturated aldehyde which possesses useful perfuming and flavoring properties. Use of said aldehyde as perfume and flavor ingredient.

2 Claims, No Drawings

PERFUMED ARTICLES CONTAINING CIS-OCT-6-EN-1-AL

This is a division of application Ser. No. 765,056, filed Feb. 2, 1977, now U.S. Pat. No. 4,132,675 issued on Jan. 2, 1979.

BACKGROUND OF THE INVENTION

Among the great variety of synthetic compounds which find a utility in the perfumery as well as the flavour industry, unsaturated aldehydes occupy a position of choice. It is known for instance that cis-hept-4-en-1-al can be used as a flavour modifier for reproducing fatty and green gustative notes, whereas trans-hex-2-en-1-al and cis-hex-3-en-1-al develop a green and pleasant character. Their fragrance properties are particularly pronounced in floral type compositions.

Trans-Oct-6-en-1-al has also been described in the scientific literature [J. Amer. Chem. Soc., 86.3759 (1964)], no mention however has been made therein as to its possible organoleptic properties nor to its possible use in the field of perfumery or flavours.

In the perfumery, increasing interest has been shown in the course of recent years for fruity, melon-like fragrance notes. Indeed, this represents a fashionable trend in modern perfumery and much effort has been devoted to the reconstitution of these types of odours.

THE INVENTION

We have now surprisingly discovered that cis-oct-6-en-1-al, a novel unsaturated aliphatic aldehyde, develops perfuming properties which considerably differ from those developed by the prior known aldehyde derivatives mentioned above. In its pure state cis-oct-6-en-1-al possesses a fresh and elegant fruity character reminiscent of the fragrance of melon associated with the freshness developed by cucumber. Consequently, the said aldehyde finds a particular utility in perfume compositions destined to be incorporated in cosmetic articles such as shampoos, deodorizers, toilet soaps and bath preparations, as well as in detergents. In the cited applications cis-oct-6-en-1-al improves, enhances or modifies the natural, fresh, green, aldehydic and fruity fragrance.

The present invention relates to a process for enhancing, improving or modifying the fragrance properties of perfumes and perfumed articles, which comprises the step of admixing cis-oct-6-en-1-al in said perfumes and perfumed articles.

The invention relates further to a perfume composition which comprises as effective fragrance modifying ingredient cis-oct-6-en-1-al.

Finally, the invention discloses a process for enhancing, improving or modifying the flavour properties of foodstuffs, beverages, pharmaceutical preparations and tobacco, which process consists in adding to the above said materials a small but flavour modifying amount of cis-oct-6-en-1-al.

The aldehyde of the invention can be used in its isolated form or more frequently in association with other perfuming coingredients, perfume bases, diluents, excipients and carriers. Its power is such that minute amounts of it can already achieve satisfactory results. Concentrations as small as 0.01 to 0.1% by weight of the total wight of the composition into which the aldehyde is incorporated may be envisaged in most of the current applications. These values however can be increased up to 1 to 2% whenever special effects are desired.

When cis-Oct-6-en-1-al is used as a flavour modifier, it develops fatty, soapy, slightly green and fruity gustative characters. Consequently, the compound of the invention finds a particularly suitable application for the aromatization of beverages such as fruit juices, puddings, pastries and desserts in general.

Its proportions can vary within a wide range; preferentially, however, concentrations of between about 0.0005 and 0.05 ppm (parts per million) by weight of the aldehyde of the invention, based on the total weight of the article into which it is incorporated, achieve the best results.

The values given above, however, are not deemed to be absolute and those skilled in the art will appreciate that concentrations higher or lower than those afore indicated may equally apply in certain circumstances.

cis-Oct-6-en-1-al is a new compound which can be synthesized starting from deca-cis,cis-2,8-diene via a process which consists in ozonizing the said olefine and reducing then the obtained ozonide according to current methods. The process followed is indicated hereinbelow. The temperature are indicated in degrees centigrade.

cis-Oct-6-en-1-al

A solution of 12.6 g (0.091 M) of deca-cis,cis 2,8-diene in 180 ml of anhydrous pentane was cooled to 15° and subjected during 45 min. to ozonisation by introducing therein a flow of ozone at a constant rate of 2.55 g of $O_3/h$.

23 g (0.087 M) of triphenylphosphine in 100 ml of anhydrous ether have then been added dropwise within 5 min. to the reaction mixture kept under stirring at about 0°/−4°, whereupon the said mixture was diluted with 50 ml of ether and the whole left at room temperature during 3h.

By steam distillation there was obtained an aqueous phase which was then extracted with ether. The combined organic extracts were subjected to the usual work-up by washing, drying and evaporating it to give 13 g of a raw material which was then purified by fractional distillation. 9.22 g of a fraction having bp. 77°-81°/25 Torr were thus collected. The product was further purified via the formation of its bisulfite derivative, which operation was carried out as follows:

9.22 g of the above obtained fractions were mixed at room temperature during 3h with 36 g of a saturated aqueous solution of $NaHSO_3$. The crystalline product thus formed was collected by filtration and washed with ether before decomposing it by warming it up on a water bath in the presence of about 20 ml of a 10% aqueous solution of $Na_2CO_3$.

The obtained mixture was extracted with ether and the combined organic extracts were worked up as usual to give a residue which upon distillation yielded 2.2 g of the desired cis-oct-6-en-1-al having bp. 115°/50 Torr. The analytical data of the thus obtained product were as follows:

IR (neat): 2710, 1725 and 700 cm$^{-1}$;

MS: M$^+$=126 (<1); m/e: 108 (13), 98 (19), 93 (26), 82 (41), 67 (88), 55 (100), 44 (22), 41 (88), 29 (47);

NMR (60 MHz): 1.6 (3H, d, J=5 cps); 2.45 (2H, t=d, $J_1 \simeq 6.5$; $J_2$=1.5 cps); 5.45 (2H, m); 9.76 (1H, d, J=1.5 cps) δ ppm.

The bisulfitic mother liquors were also extracted with ether and the operation described above was repeated to enable the recovery of 5 g of starting deca-cis,cis 2,8-diene.

Deca-cis,cis-2,8-diene can be obtained as follows:

a. 11.82 g (0.105 M) of propylene dichloride were added dropwise within 20 min. under vigorous stirring at −32° to a solution obtained by dissolving 2.33 g (0.336 atg) of lithium and 0.05 g of Fe (NO$_3$)$_3$. 9H$_2$O in about 150 ml of ammonia. The obtained mixture was kept under stirring during 40 min., whereupon, 8.75 g (0.0405 M) of butylene dibromide were added thereto over a period of 20 min. The reaction mixture was then heated to reflux temperature during 5h and diluted then with 100 ml of anhydrous tetrahydrofurane. The excess of ammonia was taken off overnight by slow distillation and the residual suspension was poured into ice-water. Extraction with ether, followed by the usual treatments on the combined organic extracts gave a residue which upon bulb distillation yielded 5.02 g (yield about 92%) of a fraction having bp. 110°–150°/11 Torr b. 6.71 g of the product obtained according to the procedure indicated above in 130 ml of anhydrous pentane were hydrogenated in the presence of 0.5 g of 5% palladium on Ba SO$_4$.

The hydrogenation was effected at room temperature and atmospheric pressure and it was completed within 2½h with a total hydrogen intake of 2.15 l. Deca-cis,cis 2,8-diene was obtained with 97% yield (6.9 g) after filtration of the reaction mixture and concentration under reduced pressure of the clear filtrate.

The invention is better illustrated by but not limited to the following examples.

EXAMPLE

A base perfume composition was prepared by mixing together the following ingredients (parts by weight):

| | |
|---|---|
| Artificial bergamot oil | 4.0 |
| Hydroxycitronellal | 1.0 |
| Methyl dihydrojasmonate | 1.0 |
| Phenylethanol | 1.0 |
| Synthetic jasmin oil | 1.0 |
| Vetiveryl acetate | 1.0 |
| | 9.0 |

By adding to 4.5 g of the above defined base composition 0.05 g of cis-oct-6-en-1-al, there was obtained a novel perfume composition possessing, by comparison with the base composition, an improved fruity character which was particularly pleasant and reminiscent of the odour of melon.

What is claimed is:

1. A process for enhancing, improving or modifying the fragrance properties of perfumed articles selected from a cosmetic or a detergent which comprises the step of admixing from 0.01% to 2% by weight of cis-oct-6-en-1-al in said perfumed articles.

2. A perfumed article selected from a cosmetic or a detergent which comprises as an effective fragrance-modifying ingredient from 0.01% to 2% by weight of cis-oct-6-en-1-al.